US008350038B2

(12) United States Patent
Beckert et al.

(10) Patent No.: US 8,350,038 B2
(45) Date of Patent: Jan. 8, 2013

(54) FLUORESCENCE QUENCHER MOLECULES

(75) Inventors: Rainer Beckert, Jena-Wogau (DE); Frank Bergmann, Iffeldorf (DE); Dieter Heindl, Paehl (DE); Rupert Herrmann, Weilheim (DE); Hans-Peter Josel, Weilheim (DE); Thomas Welzel, Jena (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 144 days.

(21) Appl. No.: 12/898,107

(22) Filed: Oct. 5, 2010

(65) Prior Publication Data

US 2011/0092689 A1    Apr. 21, 2011

(51) Int. Cl.
*C07D 217/22* (2006.01)
*C07D 217/00* (2006.01)
(52) U.S. Cl. ........................................ 546/143; 536/24.3
(58) Field of Classification Search .................. None
See application file for complete search history.

(56) References Cited

FOREIGN PATENT DOCUMENTS

| CN | 1209146 A | 2/1999 |
|---|---|---|
| CN | 1894582 A | 1/2007 |
| EP | 0313219 B1 | 5/1996 |
| WO | 84/03285 A1 | 8/1984 |

OTHER PUBLICATIONS

Rao, Koppaka V. and Beach, Joseph W., Streptonigrin and Related Compounds. 5. Synthesis and Evaluation of Some Isoquinoline Analogues, Journal of Medicinal Chemistry, 1991, pp. 1871-1879, vol. 34.
Rye, Hays S., Application of Fluorescence Resonance Energy Transfer to the GroEL-GroES Chaperonin Reaction, Methods, 2001, pp. 278-288, vol. 24.

*Primary Examiner* — Brandon Fetterolf
*Assistant Examiner* — Jean Cornet

(57) ABSTRACT

Disclosed are pyridinyl-isoquinoline-dione derivatives, methods of producing these derivatives, conjugates comprising the pyridinyl-isoquinoline dione derivatives and (i) a solid support, or (ii) a biomolecule, methods of producing these conjugates as well as the use of these conjugates as quenchers in fluorescence resonance energy transfer (FRET).

14 Claims, 1 Drawing Sheet

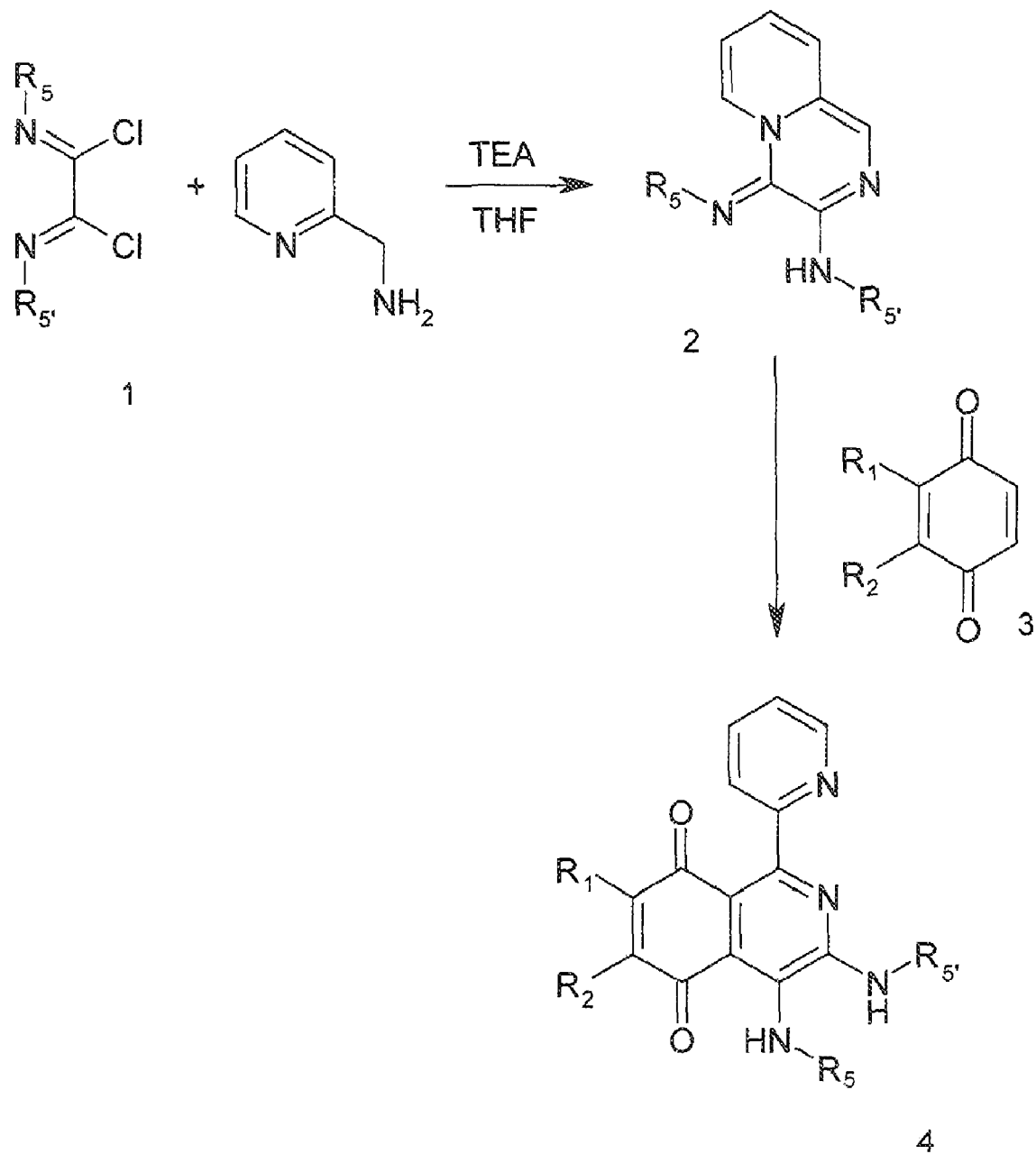

US 8,350,038 B2

FLUORESCENCE QUENCHER MOLECULES

RELATED APPLICATIONS

This application claims priority to European application EP 09013202.8 filed Oct. 20, 2009.

SEQUENCE LISTING

The instant application contains a Sequence Listing which has been submitted in ASCII format via EFS-Web and is hereby incorporated by reference in its entirety. Said ASCII copy, created on on Sep. 10, 2010, is named 26249US.txt, and is 1,696 bytes in size.

FIELD OF THE INVENTION

The present invention relates to novel pyridinyl-isoquinoline-dione derivatives, methods of producing these derivatives, conjugates comprising the novel pyridinyl-isoquinoline dione derivatives and (i) a solid support, or (ii) a biomolecule, methods of producing these conjugates as well as the use of these conjugates as quenchers in fluorescence resonance energy transfer (FRET).

BACKGROUND OF THE INVENTION

Fluorescence resonance energy transfer (abbreviated FRET), also known as Förster resonance energy transfer (named after its discoverer Theodor Forster) is a mechanism describing the transfer of excitation energy from one molecule to another without the need for fluorescence and re-absorption. According to Förster, energy transfer proceeds via dipole-dipole coupling of the donor fluorescence dipoles with the acceptor absorption dipoles. Thus, the phenomenon of FRET is always a non-radiative energy transfer. A donor chromophore, initially in its electronically excited state after having absorbed light of a certain wavelength may transfer energy radiationless to an acceptor, whereupon the acceptor is promoted to its electronically excited state. Subsequently, the electronically excited state of the acceptor decays so that in turn energy is emitted. The efficiency of FRET depends on many parameters which can be grouped as follows: the distance between the donor and the acceptor; the spectral overlap of the donor emission spectrum and the acceptor absorption spectrum; and the relative orientation of the donor emission dipole moment and the acceptor absorption dipole moment.

In conventional FRET technology donor and acceptor are both fluorophores. Accordingly, energy absorbed by a donor fluorophore as light of a certain wavelength (absorption wavelength) is transferred to the acceptor. By absorption of the transferred energy the acceptor is promoted to an electronically excited state which subsequently decays whereupon the energy transferred to the acceptor is emitted as light of a particular wavelength (emission wavelength). The emission wavelength is shifted to longer wavelength in comparison to the absorption wavelength. When donor and acceptor are in close proximity (e.g., 1-10 nm) due to the interaction of the chromophores, the acceptor emission is predominantly observed because of the FRET from the donor to the acceptor. Accordingly, the phenomenon of FRET can be detected via a decrease of donor fluorescence or an increase of acceptor fluorescence.

In a specific form of FRET a so-called quencher is applied instead of a fluorescent acceptor (J. R. Lakowicz, Principles of Fluorescence, 2nd edition, Kluwer Academic Plenum Publishers, New York, 1999). A quencher is a molecule which absorbs the energy transferred from the donor (also called reporter) but instead of in turn emitting light it quenches fluorescence. Accordingly, in a reporter-quencher system the donor transfers energy to the quencher. Thereby, the donor returns to the ground state and generates the excited state of the quencher. Subsequently, the excited state of the quencher decays non-radiatively (dark quencher). In non-radiative or dark decay, energy is given off via molecular vibrations (heat). Since the concentration of quenchers in a probe is typically in the range of µM or less, the heat of radiationless decay is too small to affect the temperature of the solution. According to the Förster equation such a fluorescence quenching also depends on the distance between donor and acceptor. In contrast to the FRET technique mentioned above not the emission of the acceptor but only the one of the donor is measured: the more the chromophores move apart from each other, the weaker the energy transfer gets so that the fluorescence of the donor correspondingly increases.

Until the last few years, quenchers have typically been fluorescent dyes, for example, fluorescein as the reporter and rhodamine as the quencher (FAM/TAMRA probes). One of the best known quenchers is TAMRA (tetramethyl-rhodamine) which is used to lower the emission of the reporter dye. Due to its properties TAMRA is suitable as quencher for FAM (carboxyfluorescein), HEX (hexachlorofluorescein), TET (tetrachloro-fluorescein), JOE (5'-Dichloro-dimethoxy-fluorescein) and Cy3-dyes (cyanine).

The usefulness of TAMRA is, however, limited because of its broad emission spectrum which reduces its capabilities in multiplexing (when two or more reporter-quencher probes are used together). Its intrinsic fluorescence contributes to the background signal which leads to decreased signal dynamics and thus, potentially reduces the sensitivity of assays based on TAMRA.

Dark quenchers offer a solution to this problem because they do not occupy an emission bandwidth. Furthermore, dark quenchers enable multiplexing. A typical dark quencher is DABCYL (4-[[4-(dimethylamino)-phenyl]-azo]-benzoic acid) which is often used in combination with molecular beacons. DABCYL quenches dyes in a range of from 380 to 530 nm. Accordingly, even fluorophors having longer wave length emission such as Cy3-dyes can be better quenched by DABCYL. However, DABCYL has an inadequate absorption band that overlaps very poorly with fluorophores emitting above 480 nm. A further non-fluorescent dye is Eclipse Quencher (4-[[2-chloro-4-nitro-phenyl]-azo]-aniline (Epoch Biosciences, Inc.) which has an absorption maximum at 530 nm and efficiently quenches over a spectrum from 520 to 670 nm.

An improvement over the dark quenchers mentioned above are the Black Hole Quenchers, such as BHQ-1 ([(4-(2-nitro-4-methyl-phenyl)-azo)-yl-((2-methoxy-5-methyl-phenyl)-azo)]-aniline) and BHQ-2 ([(4-(1-nitro-phenyl)-azo)-yl-((2,5-dimethoxy-phenyl)-azo)]-aniline) (all available from Biosearch Technologies, Inc.) which are capable of quenching across the entire visible spectrum. These non-fluorescent acceptors are often applied as alternative to fluorescent acceptors in order to decrease background fluorescence and in this way sensitivity.

The disadvantage of the known non-fluorescent quenchers is, however, their insufficient quenching behavior resulting in high background which in turn leads to limited signal dynamics.

Therefore, one object of the present invention was the provision of new quenchers, preferably with a low background signal and/or high quenching efficiency. Additionally, in a preferred embodiment they may be coupled to biomolecules or a solid support for FRET.

SUMMARY OF THE INVENTION

Surprisingly, it has been found that pyridinyl-isoquinoline-dione derivatives feature a low background signal and/or high quenching efficiency. So far, this class of substances has been described little and only for pharmaceutical applications (J. Med. Chem. 1991, 34, 1871-1879). Furthermore, diphenylamino-derivatives of this class of substances and derivatives with functional groups for coupling to biomolecules or a solid support are not known in the art.

Accordingly, the present invention relates to a compound for Formula I

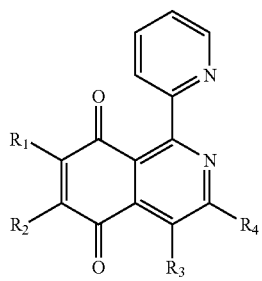

(I)

wherein one of $R_1$ and $R_2$ is hydrogen, C1-C6 alkyl or a halogen, and the other is -Q-Y, wherein Q represents a linking group comprising from 1 to 10 linearly, covalently connected atoms, and Y is a functional group, particularly wherein the Q is a straight or branched, saturated or unsaturated, substituted or unsubstituted C1-C10 hydrocarbon chain and Y is selected from the group consisting of hydroxyl, carboxyl, and amino; and $R_3$ and $R_4$ are independently from each other represented by $-NR_5R_6$, wherein $R_5$ and $R_6$ are independently from each other hydrogen or substituted or unsubstituted aryl.

BRIEF DESCRIPTION OF THE DRAWINGS

FIG. 1 illustrates the general reaction pathway for producing the compound of Formula I as described in Example 1.

DETAILED DESCRIPTION OF THE INVENTION

The term "alkyl" is used herein as known to the expert skilled in the art and refers to a univalent residue consisting only of carbon and hydrogen atoms. The alkyls form homologous series with the general formula $C_nH_{2n+1}$. The alkyl can be a straight or branched alkyl, for example the alkyl can be a secondary alkyl which is branched with the central carbon atom linked to two carbon residues or a tertiary alkyl which is branched with the central carbon atom linked to three carbon residues. The C1-C6 alkyl of formula (I) may be, e.g., methyl, ethyl, n-propyl, iso-propyl, n-butyl, iso-butyl, tert-butyl, n-pentyl, 2-pentyl, 3-pentyl, 2-methylbutyl, 3-methylbutyl, 3-methylbut-2-yl, 2-methylbut-2-yl, 2,2-dimethyl-propyl, n-hexyl, 2-methyl-pentyl, 3-methyl-pentyl, 2-dimethyl-butyl, 3-dimethyl-butyl, 4-dimethyl-butyl, 2,3-dimethylbutyl, 2,4-dimethylbutyl, or 3,4-dimethylbutyl, 2-ethylbutyl, 3-ethylbutyl, 2-methyl-pentyl, or 3-methyl-pentyl, preferably methyl, ethyl, n-propyl, iso-propyl, or tert-butyl, more preferably methyl, ethyl, or iso-propyl, and most preferably methyl.

The term "halogen" is used herein as known to the expert skilled in the art and refers to the residues fluorine, chlorine, bromine, iodine, and astatine, preferably chlorine and bromine.

The letter Q in the group -Q-Y represents a "linking group" comprising from 1 to 10 linearly, covalently connected atoms. The term "linking group" is used herein as known to the expert skilled in the art and relates to a moiety which is used in synthesis for the connection of bigger moieties. Accordingly, in a first aspect the divalent group -Q- refers to a linking group which connects the functional group Y with the pyridinyl-isoquinolin-dione moiety. In a further and more important aspect, the linking group Q refers to the later linking group in the conjugate of the present invention in which the compound of the present invention is coupled to a solid support or a biomolecule, wherein the compound is coupled to the support or the biomolecule via the linking group Q (as explained below in more detail).

Consequently, the term "linking group" in the present context also comprises the meaning of the term "linker" as known to the expert skilled in the art. For example, the linking group can be fully comprised of hydrogen and carbon atoms such that from 1 to 10 carbon atoms are linearly, covalently connected, as in form of a substituted or unsubstituted, branched or linear, saturated or unsaturated hydrocarbon chain.

In one embodiment the 1 to 10 atom chain of the linking group Q can be fully comprised of hydrogen and carbon atoms in form of a substituted or unsubstituted, branched or linear, saturated or unsaturated hydrocarbon chain.

The term "hydrocarbon chain" in context with the linking group is used herein as known to the expert and relates to an organic compound consisting entirely of carbon and hydrogen. Accordingly, in the case of the linking group being a hydrocarbon chain the linking group may be a divalent alkylene group which can be represented by the formula $-(CH_2)_n-$, wherein n is an integer ranging from 1 to 10, i.e., 1, 2, 3, 4, 5, 6, 7, 8, 9, or 10, a divalent alkenylene group with one or more carbon-carbon double bonds and, e.g., 1 to 10 carbon atoms, i.e., 1, 2, 3, 4, 5, 6, 7, 8, 9, or 10 carbon atoms, or a divalent alkynylene group with one or more carbon-carbon triple bonds and, e.g., 1 to 10 carbon atoms, i.e., 1, 2, 3, 4, 5, 6, 7, 8, 9, or 10. Accordingly, e.g., Q can be a divalent alkylene group having from 1 to 10 carbon atoms, i.e., 1, 2, 3, 4, 5, 6, 7, 8, 9, or 10, such as n-decylene, n-nonylene, n-octylene, n-heptylene, n-hexylene, n-pentylene, n-butylene, n-propylene, n-ethylene and methylene.

The hydrocarbon chain can also be branched having one or more alkyl groups, wherein the alkyl group can be methyl, ethyl, n-propyl, iso-propyl, n-butyl, iso-butyl, or tert-butyl.

Alternatively or additionally, the hydrocarbon chain can also include a cyclic component, such as a cycloalkylene or a phenylene group, wherein the term phenylene group is used known to the expert skilled in the art and relates to a divalent aromatic group $-C_6H_4-$ which is derived from benzene. The term cycloalkylene is used herein as known to the expert skilled in the art and relates to a divalent cyclic hydrocarbon residue, wherein the cycloalkylene can be cyclopropylene, cyclobutylene, cyclopentylene or cyclohexylene, preferably cyclohexylene.

Such a hydrocarbon chain can also be substituted by, e.g., halogen atoms or hydroxyl groups. Accordingly, from 1 hydrogen atom to all hydrogen atoms of the respective hydrocarbon chain can be substituted through, e.g., halogen atoms or a hydroxyl group.

The term "substituted" in context with the definition of the term linking group is used herein as known to the expert skilled in the art and relates to the substitution of a hydrogen atom of the hydrocarbon chain through a monovalent residue, such as halogen, a hydroxyl group, thiol group, amino group, methyl or ethyl group, wherein the term halogen is as defined above.

Furthermore, the term "substituted" also refers to the substitution of two hydrogen atoms through an oxygen atom under formation of a carbonyl group by substitution of two hydrogen atoms at one single carbon atom or by formation of an epoxide group by substitution of two hydrogen atoms at two adjacent carbon atoms.

Finally, the term "substituted" can also relate to the substitution of one or more, e.g., 1, 2, 3, or at most 4, methylene units ($-CH_2-$) of the hydrocarbon chain through the corresponding number of divalent atoms or atom groups, such as sulfur, oxygen, or a nitrogen containing group such as $-NH-$ or $-NR-$, wherein R is, e.g., methyl or ethyl.

Exemplary, the linking group may contain at least one ether linkage by substitution of a methylene unit though oxygen. Accordingly, the linking group may contain, e.g., at least one ethylene glycol unit of the type $-(O-CH_2-CH_2)_n-$, wherein n is an integer ranging from 1 to 3, and thus, for n=3 the linking group can be considered as a short polyethylene glycol chain. As a further example, the linking group may also contain one or two ester or amide linkages. The incorporation of at least one ester group and/or at least one amide group is recommended in order to obtain a more rigid linking group.

The term "unsubstituted" in context with the definition of the term linking group is used herein as known to the expert skilled in the art and relates to a hydrocarbon chain which fully consists of carbon and hydrogen.

The term "linear" in context with the definition of the term linking group is used herein as known to the expert skilled in the art and relates to a linking group in which members of the linking group which are at least divalent and have at least two adjacent atoms are arranged in a straight line. Accordingly, the terms "linear" and "straight" are used equivalent in the context of the present invention.

The term "linearly, covalently connected atoms" in context with the definition of the term linking group is used herein as known to the expert skilled in the art and relates to a linking group in which members of the linking group are connected through covalent bonds and wherein these covalently connected members are arranged in a straight line. The covalent bonds may be carbon-carbon single bonds, carbon-carbon double bonds, or carbon-carbon triple bonds. As a further example carbon atoms and heteroatoms such as oxygen, sulfur or nitrogen containing groups such as $-NH-$ or $-NR-$, wherein R is, e.g., methyl or ethyl, are covalently connected in a linear manner. Preferably, the term "linearly, covalently connected atoms" in context with the definition of the term linking group is a 1 to 20 atoms containing chain.

The term "branched" in context with the definition of the term linking group is used herein as known to the expert skilled in the art and refers to the presence of a side-chain at the main chain of the molecule or moiety. Accordingly, a branched linking group can be a hydrocarbon chain as defined above having one or more alkyl groups as side chain, wherein the alkyl group is methyl, ethyl, n-propyl, iso-propyl, n-butyl, iso-butyl, or tert-butyl, preferably a methyl or ethyl group. In the branched hydrocarbon chain represented by Q from one to all carbon atoms can have one or more alkyl groups as defined above.

The term "saturated" in context with the definition of the term linking group is used herein as known to the expert skilled in the art and relates to a linking group in which all members of the group are connected to the respective adjacent atom(s) through single bonds. Accordingly, a saturated hydrocarbon chain is represented by the formula $-(CH_2)n-$ with n being an integer ranging from 1 to 10. Likewise, a short polyethylene glycol chain of the type $-(O-CH_2-CH_2)n-$ or a short polyethylene sulfide chain of the type $-(S-CH_2-CH_2)n-$, wherein n is an integer ranging from 1 to 3 is saturated. Alternatively or additionally, a short polyethylene imine chain of the type $-(NH-CH_2-CH_2)n-$, wherein n is an integer ranging from 1 to 3 is also an exemplary saturated linking group.

The term "unsaturated" in context with the definition of the term linking group is used herein as known to the expert skilled in the art and refers to a linking group, e.g., a hydrocarbon chain in which not all of the carbon atoms are fully saturated with hydrogen or other atoms.

As an example, the hydrocarbon chain can have one or more double or triple bonds, wherein the term "double bond" is used herein as known to the expert skilled in the art and relates to a bond of two atoms through two electron pairs. Likewise, the term "triple bond" is used herein as known to the expert skilled in the art and relates to a bond of two atoms through three electron pairs. The linking group can have at least one double bond, accordingly, the linking group Q can be a hydrocarbon chain having one, two or more carbon-carbon double bonds. As an example, the linking group Q can be a hydrocarbon chain which is fully comprised of alternating carbon-carbon double bonds of the type $-CH=CH-CH=CH-$. Alternatively, the linking group may be fully comprised of cumulative carbon-carbon double bonds, and thus, the linking group may be represented by $-(CH=CH)n-$, wherein n is an integer ranging from 1 to 5, i.e., 1, 2, 3, 4 or 5. In another example of unsaturated hydrocarbon chains, one or both carbon atoms of the carbon-carbon double bond may have an alkyl group, wherein the term alkyl group is as defined above, preferably being methyl. In a further example, only every second carbon-carbon double bond can have one alkyl group, preferably a methyl group, comparable to the hydrocarbon chain of the carotinoids.

Further, the carbon-carbon double bonds may be independently from each other either cis or trans, respectively Z or E. The terms cis and Z with respect to the carbon-carbon double bond are used as known to the expert skilled in the art and relate to an isomer in which both substituents or hydrogen atoms, respectively, are on the same side of the double bond. The terms trans and E with respect to the carbon-carbon double bond are used as known to the expert skilled in the art and relate to an isomer in which both substituents or hydrogen atoms are each on different sides of the double bond, comparable to the hydrocarbon chain of the carotinoids.

In a further example, the hydrocarbon chain can have one or more triple bonds. Accordingly, the hydrocarbon chain can have from one up to twelve carbon-carbon triple bonds. The linking group can be fully comprised of alternating or cumulative carbon-carbon triple bonds. Also, the hydrocarbon chain simultaneously can have carbon-carbon double and carbon-carbon triple bonds. The incorporation of at least one carbon-carbon double bond and/or at least one carbon-carbon triple bond into the linking group may be desirable, if stiffening the linking group due to the missing free rotation of the carbon-carbon multiple bonds was intended.

The term "functional group" is used herein as known to the expert skilled in the art and refers to any of numerous combinations of atoms that form parts of chemical molecules, that undergo characteristic reactions themselves, and that in many cases influence the reactivity of the remainder of the molecule. Typical functional groups are hydroxyl, carboxyl, aldehyde, carbonyl, amino, azide, alkynyl, thiol and nitril. These groups can also be derivatized according to the methods as known to the expert skilled in the art. Accordingly, a functional group can also be a hydroxyl group which has been derivatized, e.g., with tosylchloride to a tosyl group which is a good leaving group in nucleophilic reactions, or the functional group can also be, e.g., a carboxylic acid halide, or an N-hydroxysuccinimide ester or a phosphoramidite. Phosphoramidites can either be directly formed by reaction with a hydroxyl group or by using trifunctional linkers (Gen Probe EP 313219). The compound of the present invention may be coupled to a biomolecule or to a solid support via the functional group.

Depending on the nature of the solid support or of the biomolecule to which the compound of the present invention shall be coupled to the functional group has to be chosen accordingly. In general, the functional group should be chosen in such a way that it matches the reactivity of the corresponding functional group of the solid support or of the biomolecule with which the functional group of the compound of the present invention is intended to react in order to form a bond. For example, if the functional group of the compound of the present invention is a nucleophilic group, such as an amino, or hydroxyl group the corresponding group of the solid support or of the biomolecule is in principle an electrophilic group, such as carbonyl, aldehyde, halogen atom, carboxylic acid halide or a carboxyl group. In a further example, a hydroxyl group as a representative nucleophilic group may be derivatized by reaction with tosylchloride or trifluor-acetic anhydride to a tosylate or a triflate group which are both excellent leaving groups in nucleophilic substitution reactions.

The term "derivatizing" is used herein as known to the expert skilled in the art and relates to a derivative of a chemical compound, wherein starting from the chemical compound the derivative is often formed in only one reaction. Thus, the derivative stands in a close chemical relationship to the starting chemical compound. Likewise, a carbonic acid NHS ester is a derivatized form of a carboxylic acid obtained through treating a carboxylic acid with N-hydroxysuccinimide and DCC (dicyclohexyl-carbodiimide). A nitrile group can be reduced to an amino group through hydrogenation on palladium on carbon as hydrogenation catalyst and either hydrogen or any hydrogen providing hydrogen source. In order to avoid any side reaction the respective derivatizing reaction should be performed prior to the coupling of the compound of the present invention with the solid support or the biomolecule.

$R3$ and $R4$ are independently from each other represented by —$NR_5R_6$, wherein $R_5$ and $R_6$ are independently from each other hydrogen or substituted or unsubstituted aryl. The term "$NR_5R_6$" is used herein as known to the expert skilled in the art and relates to a primary, secondary or tertiary amino group depending on its substituents $R_5$ and $R_6$. If both substituents $R_5$ and $R_6$ are hydrogen atoms, the respective group —$NR_5R_6$ is a primary amino group, if one of $R_5$ and $R_6$ is hydrogen and the other a substituted or unsubstituted aryl then —$NR_5R_6$ is a secondary amino group and if $R_5$ and $R_6$ are both substituted or unsubstituted aryl groups then —$NR_5R_6$ is a tertiary amino group. $R_3$ and $R_4$ are independently from each other represented by —$NR_5R_6$. Accordingly, $R_3$ and $R_4$ can each have different substituents represented by $R_5$ and $R_6$. As an example, $R_3$ can have —$NR_5R_6$ with $R_5$ and $R_6$ both being hydrogen, and $R_3$ can have —$NR_5R_6$ with $R_5$ being hydrogen and $R_6$ being an unsubstituted aryl. In a further example, $R_3$ can have —$NR_5R_6$ with $R_5$ and $R_6$ being both unsubstituted aryl while $R_5$ can have —$NR_5R_6$ with both $R_5$ and $R_6$ being substituted aryl.

The term "aryl" is used herein as known to the expert skilled in the art and refers to an aromatic residue consisting solely of hydrogen and carbon atoms, such as a phenyl ($C_6H_5$), naphthyl ($C_{10}H_7$—) or anthracenyl ($C_{14}H_9$—) residue. The aryl can be substituted or unsubstituted with, e.g., alkyl groups, such as methyl, ethyl, n-propyl, iso-propyl, n-butyl, iso-butyl, or tert-butyl; or halogen atoms, such as bromide, chloride, or fluoride.

As explained in more detail above, Y in the group -Q-Y represents a functional group. In the context of the present invention preferred functional groups are hydroxyl, carboxyl, and amino. Accordingly, in one preferred embodiment of the invention the group Y of the compound of Formula I is selected from the group consisting of hydroxyl, carboxyl, amino, azide, alkynyl, phosphoramidite, and NHS ester.

In an even more preferred embodiment of the invention the group Q of the compound of Formula I is a straight or branched, saturated or unsaturated, substituted or unsubstituted C1-C10 hydrocarbon chain, preferably C2-C8 hydrocarbon chain, more preferably C2-C5 hydrocarbon chain, still more preferably C3, C4, or C5 hydrocarbon chain, and most preferably C4 hydrocarbon chain; and/or the group Y of the compound of Formula I is a hydroxyl or carboxyl group.

The term "hydrocarbon" is used herein as known to the expert skilled in the art and refers to an organic residue consisting entirely of hydrogen and carbon atoms. The term "chain" in addition to the term "hydrocarbon" is used herein in its common sense and in context with the term "hydrocarbon" refers to non-cyclic hydrocarbon residues. In context with the compound of Formula I the hydrocarbon chain, represented by Q, is connected to the pyridinyl-isoquinolinedione derivative with its one end and is terminated by the functional group Y at its other end. The hydrocarbon chain can be straight or branched.

The term "saturated" in context with the hydrocarbon chain is used herein as known to the expert skilled in the art and refers to a saturated hydrocarbon chain which consists entirely of a carbon backbone with single bonds which are saturated with hydrogen bonds. The term "unsaturated" in context with the hydrocarbon chain is used herein as known to the expert skilled in the art and refers to an unsaturated chain having one or more double or triple bonds between the carbon atoms. The term "substituted" in context with the "hydrocarbon chain" is used herein as known to the expert skilled in the art and refers to a hydrocarbon chain in which one or more hydrogen atoms are replaced by, e.g., one or more halogen atoms, or one and more hydroxyl groups or one or more linear or branched C1-C4 alkyl group, such as methyl, ethyl, n-propyl, iso-propyl, n-butyl, iso-butyl, or tert-butyl.

In another preferred embodiment of the invention $R_3$ and/or $R_4$ of Formula I of the present invention is/are —$NR_5H$, preferably wherein R5 is a substituted or unsubstituted phenyl residue. Accordingly, in one case $R_3$ and $R_4$ are both —$NR_5H$ and in the other case $R_3$ or $R_4$ is —$NR_5H$. Furthermore, $R_5$ preferably is a phenyl group. The term "phenyl" is used herein as known to the expert skilled in the art and relates to a residue which is derived from the benzene residue, and therefore refers to the chemical group $C_6H_5$.

In a preferred embodiment of the invention each of $R_3$ and $R_4$ of the compound of Formula I is —$NR_5R_6$, preferably —$NR_5H$. Accordingly, $R_3$ and $R_4$ of the compound of Formula I preferably are —$NR_5H$.

In a more preferred embodiment of the invention each of $R_3$ and $R_4$ of the compound of Formula I is —$NR_5R_6$, preferably —NR$_5$H, wherein R$_5$ is unsubstituted or substituted aryl, preferably substituted with C1-C4 alkyl, more preferably substituted with methyl. Accordingly, R$_3$ and R$_4$ preferably are —NR$_5$H with R$_5$ being either unsubstituted aryl or methyl substituted aryl.

In a still more preferred embodiment of the invention R$_3$ and/or R$_4$ of the compound of Formula I is/are —NR$_5$H, wherein R$_5$ is an unsubstituted or substituted phenyl or toluyl residue. The phenyl residue can be substituted by an alkyl group, such as a methyl, ethyl, n-propyl, iso-propyl, n-butyl, iso-butyl, or tert-butyl. Accordingly, the substituted phenyl may be a toluyl.

In another preferred embodiment of the invention aryl is an aromatic C$_6$H$_5$, C$_{10}$H$_7$, or C$_{14}$H$_9$ hydrocarbon residue, such as phenyl, naphthyl, or anthracenyl, preferably an aromatic C$_6$H$_5$ or C$_{10}$H$_7$ hydrocarbon residue, and more preferably an aromatic C$_6$H$_5$ hydrocarbon residue. Accordingly, the phenyl, naphthyl, or anthracenyl residue can be unsubstituted or substituted with halogen atoms, such as bromine, chlorine, or fluorine, preferably bromine or chlorine, or with alkyl groups, such as methyl, ethyl, n-propyl, iso-propyl, n-butyl, iso-butyl or tert-butyl. Still more preferred are alkyl substituted phenyl groups, such as toluyl.

In yet another preferred embodiment of the invention one of R$_1$ and R$_2$ is a 1-hydroxy-4-ethyl-butyl residue or an n-pentanoic residue and the other is hydrogen; and R$_5$ is a 4-toluyl or a phenyl residue. Still more preferred are compounds wherein one of R$_1$ and R$_2$ is a 1-hydroxy-4-ethyl-butyl residue and the other is hydrogen, and R$_5$ is a 4-toluyl residue; or one of R$_1$ and R$_2$ is a 1-hydroxy-4-ethyl-butyl residue and the other is hydrogen, and R$_5$ is phenyl; or one of R$_1$ and R$_2$ is an n-pentanoic acid residue and the other is hydrogen, and R$_5$ is a 4-toluyl residue; as defined in the examples.

The term "1-hydroxy-4-ethyl-butyl residue" is used herein as known to the expert skilled in the art and refers to a hydrocarbon chain of the type HO—(CH$_2$)$_3$CH(C$_2$H$_5$)— which is connected with its 4-position to the quinoline-dione moiety of the compound of Formula I.

The term "4-toluyl residue" is used herein as known to the expert skilled in the art and refers to the group —C$_6$H$_4$(CH$_3$), derived from toluene, and which in context of the present invention is connected to the nitrogen atom of the —NR$_5$R$_6$ group of R$_3$ and R$_4$ at its 1-position.

The term "n-pentanoic acid residue" is used herein as known to the expert skilled in the art and refers to a straight residue of the type —(CH$_2$)$_4$—COOH which is derived from n-pentanoic acid, also known as n-valerie acid.

To observe the phenomenon of FRET, the donor and the acceptor, respectively the quencher, have to be brought into close proximity. Therefore, the non-fluorescent quencher can be attached to the biomolecule or a solid support via a linker arm, such as the linking Q moiety as defined above. The length of each linker arm can be important, as the linker arm will affect the distance between donor and acceptor moieties. The length of a linker arm for the purpose of the present invention is the distance in Angstroms from the quencher to the biomolecule or the solid support. The linker arm may be of the kind described in WO 84/03285. Also disclosed in WO 84/03285 and EP 313219 are methods for attaching linker arms to particular nucleotide bases, and also for attaching fluorescent moieties to a linker arm.

Accordingly, in one preferred embodiment of the invention Y is capable of binding to (i) a solid support, preferably a carrier, a bead, or a disc; or (ii) a biomolecule, preferably a nucleic acid, or a protein.

The term "solid support" is used herein as known to the expert skilled in the art and refers to any insoluble and inert inorganic or organic material, preferably inorganic material, preferably having a large surface area to which surface organic molecules can be attached through bond formation or absorbed through electronic or static interactions such as through bond formation through the functional group Y as defined above. Representative examples of a "solid support" in context with the present invention are silicates, such as SiO$_2$ resin, such as ion-exchange resins, glass, dextranes, celluloses or hydrophilic or hydrophobic polymers.

The term "carrier" is used herein as known to the expert skilled in the art and refers to a usually inactive substance that acts as a solid support for the compound of the invention.

The term "bead" is used herein as known to the expert skilled in the art and refers to any essentially spherical small object made of inorganic or organic material which can be charged and/or magnetized preferably having a large surface area to which surface organic molecules can be attached through bond formation or absorbed through electronic or static interactions. Representative examples of a "bead" in context with the present invention may be made of silicates, such as SiO$_2$ resin, such as ion-exchange resins, glass, dextrans, celluloses or hydrophobic or hydrophilic polymers.

The term "disk" is used herein as known to the expert skilled in the art and refers to any thin, flat plate or object having a surface that is flat and approximately round, preferably having a large surface area to which surface organic molecules can be attached through bond formation or absorbed through electronic or static interactions. Representative examples of a "disc" in context with the present invention may be made of silicates, such as SiO$_2$ resin, such as ion-exchange resins, glass, dextrans, celluloses or hydrophobic or hydrophilic polymers.

The term "carrier" is used herein as known to the expert skilled in the art and refers to a usually inactive substance that acts as a vehicle for an active substance.

The term "biomolecule" is used herein as known to the expert skilled in the art and refers to any organic molecule that is produced by a living organism or to any artificially produced derivatives of such compounds, including large polymeric molecules such as proteins, polysaccharides, carbohydrates, lipids, nucleic acids and oligonucleotides as well as small molecules such as primary metabolites, secondary metabolites, and natural products.

The term "nucleic acid" is used herein as known to the expert skilled in the art and refers to a macromolecule composed of chains of monomeric nucleotides, wherein each nucleotide consists of three components: a nitrogenous heterocyclic base, which is either a purine or pyrimidine; a pentose sugar; and a phosphate group. The term "protein" is used herein as known to the expert skilled in the art and refers to organic compounds made of amino acids arranged in a linear chain and joined together by peptide bonds between the carboxyl and amino groups of adjacent amino acid residues. Peptides are also enclosed.

Furthermore, the present invention relates to a method of producing a compound of Formula II

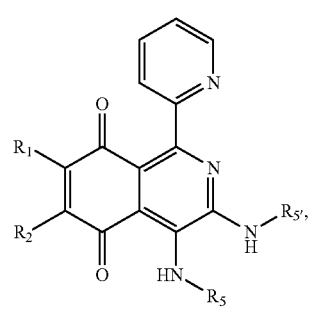

(II)

the method comprising the steps of:
a) reacting a disubstituted oxalic acid diamide of the formula R$_5$—N=C(OH)—C(OH)=N—R$_5$, with phosphorous pentachloride to obtain a bis-imidoyl chloride of oxalic acid of the formula

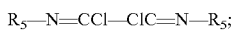

b) reacting the bis-imidoyl chloride of oxalic acid obtained in step a) with 2-amino methylpyridine to obtain a disubstituted pyrido[1,2-a]pyrazine of Formula III

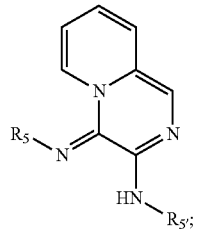

and
c) reacting the disubstituted pyrido[1,2-a]pyrazine obtained in step b) with a mono-substituted quinone of Formula IV

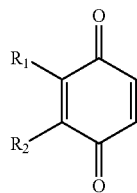

to obtain the compound of Formula II,
wherein $R_1$, $R_2$, $R_5$ are as defined as detailed above for the compound of the present invention, as far as applicable, and
wherein $R_5$, is defined as $R_5$ as defined as detailed above for the compound of the present invention, as far as applicable.

In step a) of the above detailed method of producing a compound of Formula II typically, 1 equivalent of a disubstituted oxalic acid diamide of the formula $R_5$—N=C(OH)—C(OH)=N—$R_5$, wherein $R_5$, is defined as $R_5$ as defined as detailed above for the compound of the present invention, as far as applicable is suspended with approximately 2 equivalents of phosphorous pentachloride in dry toluene and the suspension is refluxed until a clear dark yellow solution is obtained and the gas evolution is completed. After completion of the gas evolution the solvent is evaporated in vacuo and the residue is recrystallized from, e.g., n-heptane to obtain a bis-imidoyl chloride of oxalic acid of the formula

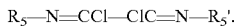

In step b) 1 equivalent of 2-amino methylpyridine together with approximately 2 equivalents of triethylamine is dissolved in THF and the obtained solution is mixed, e.g., dropwise with a solution of approximately 1 equivalent of the corresponding bis-imidoyl chloride of oxalic acid as obtained in step a). Then the obtained solution is refluxed for, e.g., approximately 4 hours and after cooling-down of the solution the solvent is evaporated in vacuo. The residue is washed with, e.g., few methanol and then the residue is recrystallized from acetonitrile or THF to yield the disubstituted pyrido[1,2-a]pyrazine of Formula III.

In step c) 1 equivalent of the mono-substituted quinone of Formula IV and approximately 1 equivalent of the pyrido[1,2-a]pyrazine of Formula III as obtained in step b) are dissolved in, e.g., dried methylenechloride. The obtained solution can, e.g., either be refluxed for typically from 5 to 12 hours or the solution can be stirred at room temperature for typically from 2 to 3 days. Reaction progress can be monitored e.g., using thin layer chromatography. After completion of the reaction the reaction mixture is evaporated to dryness and purified, e.g., using column chromatography on silica gel (eluting with, e.g., toluene/acetic acid ester or chloroform/methanol) to obtain the compound of Formula II. The formation of two regioisomers is observed, the residues $R_1$ and $R_2$ are permutated. Alternatively, the reaction can also be performed in toluene. The reaction proceeds faster in this solvent, however, simultaneously an increased amount of by-products is observed.

Preferred examples are also exemplified in the Examples below.

Biomolecules having a quencher as detailed above are of particular interest as a modern tool in FRET assays. In this context, the term biomolecule is used herein as explained above. In a representative FRET assay the binding of two molecules or polymers such as an enzyme and a substrate can be investigated. In such a process a fluorophore and a quencher are connected to particular parts of the two molecules of polymers. Upon absence of an emission spectrum of the fluorophore due to quenching involving the FRET mechanism the formation of the respective complex can be detected. Likewise, the specific action of biomolecules can be further investigated using FRET quenchers. This example is further illustrated on the basis of the closing of the so-called chaperones which are barrel-shaped "reaction vessels" in which specific proteins are folded (see H. S. Rye, Methods 24 (2001), 278). The "vessel" (GroEL) has a "cap" (GroES) which is put on the vessel in an ATP dependent process. GroEL has been provided with a fluorophore and GroES has been provided with a quencher. In the presence of ATP the fluorescence spectrum of the sample containing the chaperone significantly changes due to quenching involving FRET. In the absence of ATP the emission spectrum of the fluorophore is measured while in the presence of ATP when the "vessel" is closed with the "cap" and thus, fluorophore and quencher are in close proximity to each other, the fluorescence of the fluorophore is at least partially and ideally totally quenched.

FRET technology can also be applied for designing oligonucleotides to be used as (hybridization) probes. Designing oligonucleotides to be used as (hybridization) probes can be performed in a manner similar to the design of primers, although the members of a pair of probes preferably anneal to an amplification product within few, e.g., no more than 5 nucleotides of each other on the same strand such that fluorescent resonance energy transfer (FRET) can occur (e.g., within no more than 1, 2, 3, or 4 nucleotides of each other). This minimal degree of separation typically brings the respective fluorescent moieties into sufficient proximity so that FRET occurs. In addition, probes can be designed to hybridize to targets that contain a mutation or polymorphism, thereby allowing differential detection of for example specific nucleic acids based on either absolute hybridization of different pairs of probes corresponding to for example each particular type of nucleic acid to be distinguished or differential melting temperatures of for example, members of a pair of probes and each amplification product generated from for example a specific nucleic acid.

As used herein, "amplifying" refers to the processes of synthesizing nucleic acids that are complementary to one or both strands of a template nucleic acid. Amplifying a nucleic acid typically includes denaturing the template nucleic acid, annealing primers to the nucleic acid at a temperature that is below the melting temperatures of the primers, and enzymatically elongating the primers to generate an amplification product. The denaturing, annealing and elongating steps each can be performed once. Generally, however, the denaturing, annealing and elongating steps are performed multiple times such that the amount of amplification product is increasing, often times exponentially. Amplification typically requires the presence of deoxyribonucleoside triphosphate, a DNA polymerase enzyme (e.g., Taq polymerase) and an appropriate buffer and/or co-factors for optimal activity of the polymerase enzyme (e.g., $MgCl_2$ and/or KCl).

A common format of nucleic acid based FRET technology utilizes two hybridization probes, wherein one probe is labeled with a fluorophore and the other probe is labeled with a quencher and wherein the probes are generally designed to hybridize in close proximity to each other in a target DNA molecule (e.g., an amplification product). However, an alternative FRET format utilizes hydrolysis probes to detect the presence or absence of an amplification product. This technology utilizes one single-stranded hybridization probe labeled with one fluorescent moiety and one quenching moiety. When the fluorescent moiety is excited with light of suitable wavelength the absorbed energy is transferred to the quencher according to the principles of FRET whereupon fluorescence is quenched. During the annealing step of the PCR (polymerase chain reaction), the labeled hydrolyzation probe binds to the target DNA (i.e., the amplification product) and is degraded by the 5' to 3' exonuclease activity of the Taq Polymerase during the subsequent elongation phase. As a result, the excited fluorescent moiety and the quenching moiety become spatially separated from each other. As a consequence, upon excitation of the fluorophore when no quencher is in close proximity, the fluorescence emission can be detected. By way of example, an ABI PRISM 7700 Sequence Detection System (Life Technologies, Inc.) uses hydrolysis probe technology.

A further format also involving fluorescence resonance energy transfer is the so-called LIGHTCYCLER HYB-PROBE (Roche Diagnostics GmbH). In this technology two sequence-specific oligonucleotide probes are labeled with different dyes (donor and acceptor), and are added to the reaction mix along with the PCR primers. During the annealing phase, HYBPROBE probes hybridize to the target sequences on the amplified DNA fragment in a head-to-tail arrangement, thereby bringing the two dyes close to each other. The donor dye (fluorescein) is excited by the blued LED. As long as the two dyes are close to each other (15 nucleotides), the energy emitted by the donor dye excites the acceptor dye on the second HYBPROBE, which then emits fluorescent light at a different wavelength. This fluorescence is directly proportional to the amount of target DNA generated during PCR. HYBPROBE probes are displaced during the elongation and denaturation steps.

Accordingly, fluorescein or JA270 as donor and the fluorescence quencher molecules of the present invention as acceptor can be used in technologies involving FRET, such as the technology explained above.

Molecular beacons in conjunction with FRET can also be used to detect the presence of an amplification product using the real-time PCR methods. Molecular beacons technology uses a hybridization probe labeled with a fluorophore and a quencher, wherein the labels are typically located at each end of the probe. Molecular beacon technology uses a probe oligonucleotide having sequences that permit secondary structure formation (e.g., a hairpin). As a result of secondary structure formation within the probe, fluorophore and quencher are in spatial proximity when the probe is in solution. After hybridization to the target nucleic acids (i.e., amplification products), the secondary structure of the probe is disrupted and the fluorophore and the quencher become separated from each other and thus, after excitation with light of a suitable wavelength, the emission of the fluorophore can be detected.

Finally, since the efficiency of FRET significantly depends on the distance between fluorophore and quencher it can be applied for determining the distance between two specific areas in a particular molecule, wherein one area has been labeled with a fluorophore and the other area has been labeled with the quencher.

Due to the disadvantages of known quencher conjugates there is a need for a conjugate comprising a quencher suitable for FRET assays and a biomolecule.

Further, there is also a need for a conjugate comprising a quencher suitable for FRET assays and a solid support, in order to facilitate the separation of the quencher from a solution, for example from the solution of a probe. In this context, a conjugate comprising the compound of the present invention and a solid support is beneficial with respect to separation methods, such as filtration or separation involving migration in an electric field or separation involving charged particles in a magnetic field.

Accordingly, the compound of the present invention can also be part of a conjugate comprising the compound of the present invention and a solid support. As detailed above the compound of the present invention contains the group -Q-Y, wherein Q is a linking group and Y is a functional group. Likewise, as detailed above, the functional group Y which is connected to the linking group Q can react with a matching functional group of the solid support or the biomolecule to form a new bond. Through this newly formed bond, the linking group connects the compound of the present invention with the solid support or with the biomolecule.

Therefore, the present invention also relates to a conjugate comprising the compound according to the present invention and (i) a solid support, preferably a carrier, a bead, or a disc; or (ii) a biomolecule, preferably a nucleic acid, or a protein, wherein the compound is coupled to the support or the biomolecule via the linking group Q.

The terms "solid support", "carrier", "bead", "disc", "biomolecule", and the "functional group Y" in context with the conjugate of the present invention may be as defined above in the context of preferred embodiments of the compound of the present invention.

Further, in order to obtain the conjugate of the present invention comprising the compound of the invention and (i) a solid support, preferably a carrier, a bead, or a disc; or (ii) a bio-molecule, preferably a nucleic acid, or a protein, there is a need for producing the conjugates of the present invention.

Accordingly, the present invention also relates to a method of producing the conjugate according to the present invention, comprising binding a compound of the present invention to (i) a solid support, preferably a carrier, a bead, or a disc; or (ii) a biomolecule, preferably a nucleic acid, or a protein.

The terms "solid support", "carrier", "bead", "disc", "biomolecule", "nucleic acid" and "protein" in context with the method of the present invention of producing the conjugate according to the present invention are as defined above.

Since the conjugate comprises the compound of the present invention which can be used as a quencher the conjugate itself can also be used as a quencher. Accordingly, the conjugate comprising the compound of the present invention and (i) a biomolecule, preferably a nucleic acid, or a protein; or (ii) a solid support, preferably a carrier, a bead, or a disc can be used as a quencher of a fluorescent donor.

Therefore, the invention also relates to the use of a compound according to the present invention or of a conjugate comprising the compound of the present invention and (i) a solid support, preferably a carrier, a bead, or a disc; or (ii) an organic molecule, preferably a nucleic acid, or a protein, wherein the compound is coupled to the support or the organic molecule via the linking group Q as a quencher of a fluorescent donor.

Since the conjugate of the present invention comprising the compound of the present invention and (i) a solid support, preferably a carrier, a bead, or a disc; or (ii) a biomolecule, preferably a nucleic acid, or a protein can be used as a quencher of a fluorescent donor, this conjugate can also be used as a quencher in fluorescence resonance energy transfer (FRET).

Accordingly, the present invention also relates to the use of a conjugate comprising the compound according to the present invention and (i) a solid support, preferably a carrier, a bead, or a disc; or (ii) a biomolecule, preferably a nucleic acid, or a protein, wherein the compound is coupled to the support or the organic molecule via the linking group Q, wherein the conjugate is used as a quencher in fluorescence resonance energy transfer (FRET), e.g., as detailed above.

EXAMPLE 1

Production of Exemplary Quencher Compounds

The reaction scheme in FIG. 1 illustrates the general reaction pathway for producing the compound of Formula I.

Preparation of Bis-Imidoylchloride of Oxalic Acid (1):

Oxalic acid diamide (20 mmol) was suspended with phosphorous pentachloride (40 mmol) in dried toluene (200) and refluxed until a clear dark yellow solution was obtained and the gas evolution was completed. After completion of the reaction the solvent was removed under reduced pressure and the residue was recrystallized from n-heptane.

Pyrido[1,2-a]pyrazine (2):

2-aminomethyl pyridine (10 mmol) was dissolved together with triethylamine (20 mmol) in THF (50 ml) and a solution of the corresponding bis-imidoylchloride (10 mmol) was added dropwise. Then the solution was refluxed for ca. 4 h and after cooling-down the solvent was removed under reduced pressure. The residue was washed with little cold methanol and subsequently, the residue was recrystallized from acetonitrile or THF.

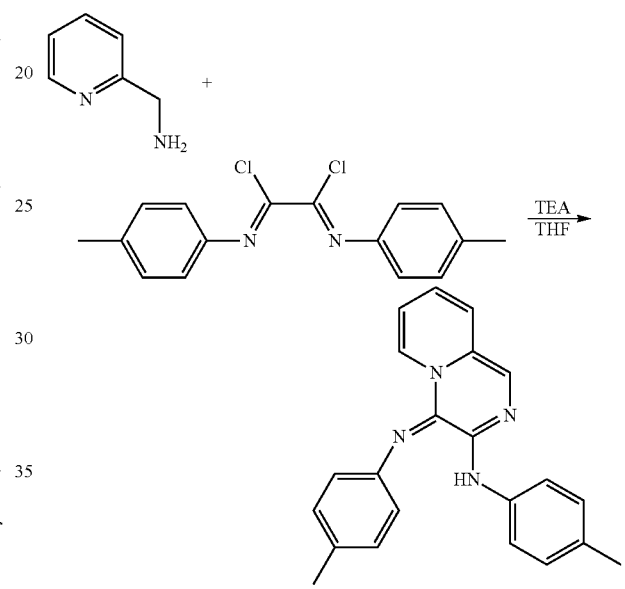

Reacting the Quinoline Component with Pyrido[1,2-a]pyrazine (4a/b):

Quinone (1 equivalent) and pyrido[1,2-a]pyrazine (1 equivalent) were dissolved in dried dichloromethane (no inert atmosphere) (ca. 30 ml solvent/1 mmol quinone) and either refluxed for several hours (typically 3-12 h) or stirred at room temperature (typically 2-3 d). Progress of the reaction was monitored using thin layer chromatography. After completion of the reaction the reaction mixture was concentrated to dryness and was purified using column chromatography ($SiO_2$/toluene: ethyl acetate or chloroform/methanol). Two regioisomers, e.g., TWDQ 9 A and B were formed.

Alternatively, the reaction was performed in toluene, wherein the reaction proceeded faster, however a higher amount of by-products was observed.

| Compound | $R_1$ | $R_2$ | $R_5 = R_{5'}$ |
|---|---|---|---|
| 4a (TWDQ9 A) | $(CH_2)_4COOH$ | H | 4-toluyl |
| 4b (TWDQ9 B) | H | $(CH_2)_4COOH$ | 4-toluyl |
| 4c (TWDQ11 A) | $(CH_2)_4COOH$ | H | phenyl |
| 4d (TWDQ11 B) | H | $(CH_2)_4COOH$ | phenyl |
| 4e (TWDQ8 A) | $CH(CH_2CH_3)(CH_2)_3COOH$ | H | 4-toluyl |
| 4f (TWDQ8 B) | H | $CH(CH_2CH_3)(CH_2)_3COOH$ | 4-toluyl |
| 4g (TWDQ10 A) | $CH(CH_2CH_3)(CH_2)_3COOH$ | H | phenyl |
| 4h (TWDQ10 B) | H | $CH(CH_2CH_3)(CH_2)_3COOH$ | phenyl |

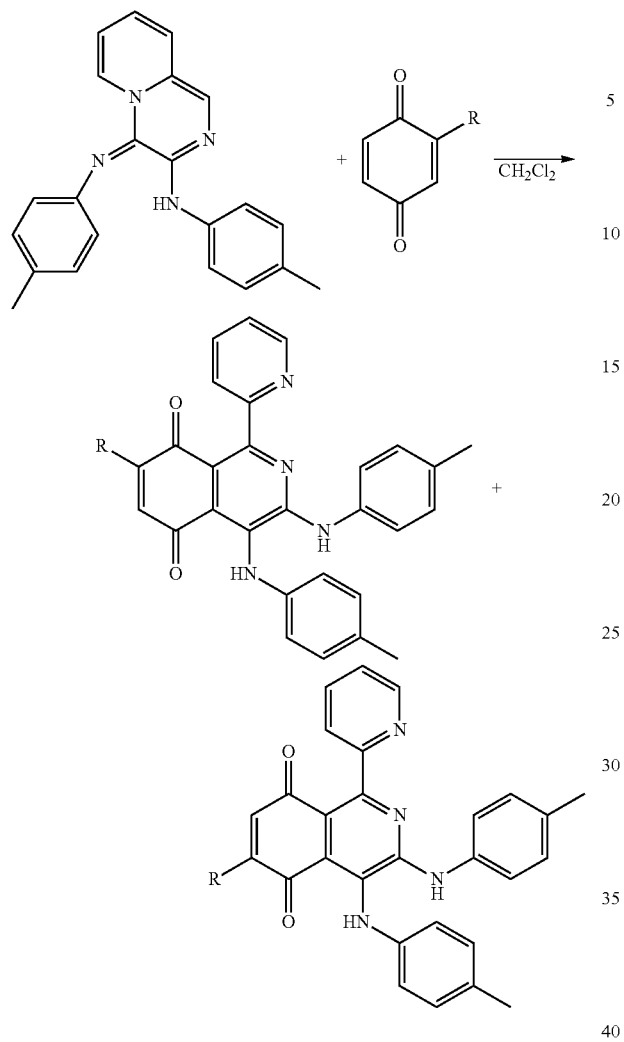

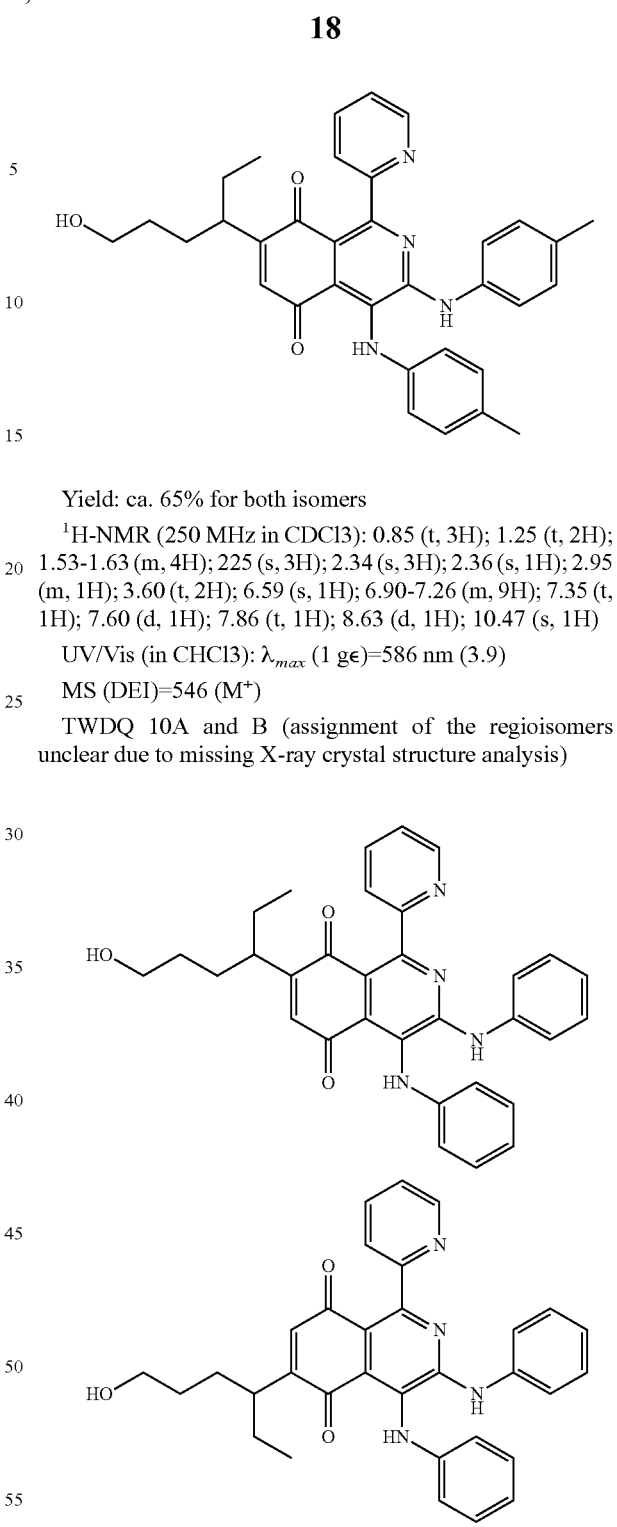

Yield: ca. 65% for both isomers $^1$H-NMR (250 MHz in CDCl3): 0.85 (t, 3H); 1.25 (t, 2H); 1.53-1.63 (m, 4H); 225 (s, 3H); 2.34 (s, 3H); 2.36 (s, 1H); 2.95 (m, 1H); 3.60 (t, 2H); 6.59 (s, 1H); 6.90-7.26 (m, 9H); 7.35 (t, 1H); 7.60 (d, 1H); 7.86 (t, 1H); 8.63 (d, 1H); 10.47 (s, 1H)

UV/Vis (in CHCl3): $\lambda_{max}$ (1 g$\epsilon$)=586 nm (3.9)

MS (DEI)=546 (M$^+$)

TWDQ 10A and B (assignment of the regioisomers unclear due to missing X-ray crystal structure analysis)

2-(Ω-Carboxy-Butyl)-1,4-Benzoquinone: Precursor for TWDQ 9

A solution of ammonium peroxodisulfate (27 mmol) in 25 ml water was added dropwise under vigorous stirring within 45 min at a temperature of 60-65° C. to a solution of 1,4-benzoquinone (20 mmol), adipinic acid (40 mmol) and silver nitrate (6 mmol) in 40 ml water. Stirring was continued for 10 minutes and then the solution was cooled down to 0° C., filtered and the residue was extracted with benzene in a Soxhlet apparatus.

Yield: ca. 35-40%, literature: 42% melting point: 108-109° C.

2-(1-Ethyl-4-Hydroxybutyl)-1,4-Benzoquinone: Precursor for TWDQ 10 and TWDQ 8

While stirring at 60° C., a solution of sodium peroxodisulfate (0.01 mol) in water (10 ml) was added to a heterogeneous mixture of silver nitrate (0.2 g) in water (40 ml) and 1,4-benzoquinone (0.01 mol) and 1-hexanol (0.04 mol) in hexane (5 ml). Extraction with diethyl ether followed by vaporization in vacuo yielded a residue which was purified using column chromatography on silica gel (eluting with hexane/diethyl-ether).

Isoquinoline-Quinones:

TWDQ 8B (assignment of the regioisomers unclear due to missing X-ray crystal structure analysis)

TWDQ 10A

Yield: ca. 25%

$^1$H-NMR (250 MHz in CDCl3): 0.70 (t, 3H); 0.83 (d, 2H); 1.51-1.61 (m, 4H); 2.36 (s, 1H); 2.88 (m, 1H); 3.51 (t, 2H); 6.64 (s, 1H); 3.90-7.30 (m, 12H); 7.67 (d, 1H); 7.88 (t, 1H); 8.56 (d, 1H); 70.27 (s, 1H)

UV/Vis (in CHCl3): $\lambda_{max}$ (1 g$\epsilon$)=550 nm (3.9)

MS (DEI)=518 (M$^+$)

TWDQ 10B

Yield: ca. 40%

$^1$H-NMR (in CDCl3): 0.84 (t, 3H); 0.90 (d, 2H); 1.51-1.61 (m, 4H); 2.37 (s, 1H); 2.88 (m, 1H); 3.51 (t, 2H); 6.61 (s, 1H); 7.00-7.39 (m, 12H); 7.63 (d, 1H); 7.86 (t, 1H); 8.63 (d 1H); 10.35 (s, 1H)

UV/Vis (in CHCl3): $\lambda_{max}$ (1 g$\epsilon$)=555 nm (3.9)

MS (DEI)=518 (M$^+$)

TWDQ 9A and B (assignment of the regioisomers unclear due to missing X-ray crystal structure analysis)

TWDQ 9A

Yield: ca. 20%

$^1$H-NMR (250 MHz in CDCl3): 1.27 (m, 2H); 1.64 (m, 2H); 2.26 (s, 3H); 2.30 (s, 3H); 2.34 (m, 2H); 2.47 (m, 2H); 6.65 (s, 1H); 6.90-7.30 (m, 9H); 7.42 (t, 1H); 7.72 (d, 1H); 7.95 (t, 1H); 8.76 (d, 1H); 10.45 (s, 1H)

UV/Vis (in CHCl3): $\lambda_{max}$ (1 g$\epsilon$)=558 nm (3.9)

MS (DEI)=546 (M$^+$)

TWDQ 9B

Yield: ca. 35%

$^1$H-NMR (250 MHz in CDCl3): 1.26 (m, 2H); 1.60 (m, 2H); 2.24 (s, 3H); 2.28 (s, 3H); 2.31 (m, 2H); 2.45 (m, 2H); 6.60 (s, 1H); 6.90-7.25 (m, 9H); 7.35 (t, 3H); 7.60 (d, 1H); 7.85 (t, 1H); 8.64 (d, 1H); 10.41 (s, 1H)

UV/Vis (in CHCl3): $\lambda_{max}$ (1 g$\epsilon$)=568 nm (3.9)

MS (DEI)=546 (M$^+$)

TWDQ 9-NHS ester

The educt is dissolved in DMF (25 mg in 3 ml) and 6 mg N-hydroxysuccinimide, 15 mg HBTU and 11 µl of morpholino-ethyl-isocyanide are added. The solution is stirred for 3 h. After evaporation the crude mixture is purified by preparative HPLC. Yield: 81%

EXAMPLE 2

Use of Exemplary Quencher Compounds in FRET Assay

Quenching efficiency of TWDQ9 was assessed in a Lambda DNA real-time PCR assay applying hydrolyses probe detection technology.

Synthesis of Lambda DNA Primers

Primers were synthesized on an ABI 394 DNA synthesizer (Life Technologies, Inc.) in 1 µmol scale using standard phosphoramidite chemistry (all reagents are available, for example, from Sigma-Aldrich or Glen Research). The primers were deprotected with ammonium hydroxide at 55° C. for 8 hours. The ammoniacal solution was evaporated and the crude oligonucleotide was purified using a strong anion exchange HPLC column with a linear gradient of sodium chloride, at high pH. Fractions containing the product oligonucleotide were pooled, desalted and formulated in 10 mM Tris, pH 8.0. Purity and optical density were determined.

```
                                      (SEQ ID NO: 1)
Lambda fwd primer      AACAAAAACGGGGTTTACCTTA (SEQ ID NO: 2)
Lambda rev primer      GTCGCTTTTTGCTGTCCCACAGTA
```

Synthesis of Lambda DNA BHQ2 Quenched Hydrolysis Probe (Reference)

Hydrolysis probes were synthesized on an ABI 394 DNA Synthesizer in 1 µmole scale using standard phosphoramidite chemistry. Besides standard dT phosphoramidite tac-dA, tac-dC and tac-dG protected deoxynucleotide phosphoramidites (Sigma-Aldrich, Cat. no. T111031, A112031, C112031, G112031) were used. In addition, JA270 phosphoramidite (Roche Applied Science, material no. 4906802) label and Black Hole Quencher (BHQ-2) quencher (Biosearch Technologies Inc., Cat. no. BNS-5052) were incorporated using phosphoramidite reagents. The 3'-phosphate was introduced by means of 3'-Extension Blocker CPG (Clontech Inc., Cat. no. PT3357-2). The oligonucleotide was deprotected with ammonium hydroxide at ambient temperature overnight. The ammoniacal solution was evaporated and the crude oligonucleotide was purified using reversed phase HPLC with a gradient of increasing amount of acetonitrile in 0.1 M triethylammonium acetate pH 7 buffer. Fractions containing the product oligonucleotide were pooled, desalted and formulated in 10 mM Tris, pH 8.0. Purity and optical density were determined.

```
                                      (SEQ ID NO: 3)
Lambda probe 1
5'- JA270 TCG GTA CGG ATA CCG CGA AAG AGC

BHQ2 PO4 -3'
```

Synthesis of Lambda DNA TWDQ9 Quenched Hydrolysis Probes

Hydrolysis probes were synthesized on an ABI 394 DNA Synthesizer in 1 µmole scale using standard phosphoramidite chemistry. Besides standard dT phosphoramidite tac-dA, tac-dC and tac-dG protected deoxynucleotide phosphoramidites (Sigma-Aldrich, Cat. no. T111031, A112031, C112031, G112031), TFA-protected 3'-aminomodifier phosphoramidite (preparation of 3-amino-1,2-propanediol based aminomodifier phosphoramidite acc. to U.S. Pat. No. 6,031,091). In addition, FAM (5'-fluorescein phosphoramidite, Glen Research, Cat. no. 10-5901) or JA270 phosphoramidite (EP 0 962 497) labels were incorporated at the 5'-terminus. The 3'-phosphate was introduced by means of 3'-Extension Blocker CPG support (Clontech Inc., Cat. no. PT3357-2). The oligonucleotides were deprotected with ammonium hydroxide at ambient temperature overnight. The ammoniacal solutions were evaporated, and the crude oligonucleotides were purified using reversed phase HPLC with a gradient of increasing amount of acetonitrile in 0.1 M triethylammonium acetate pH 7 buffer. The main peak containing fractions were collected, desalted and evaporated. Amino-modified oligonucleotides were dissolved in 0.1 M sodium borate buffer, pH 8.5 and 2×2 mg of TWDQ9-NHS ester dissolved in DMF were added (the second portion after 5 h). After reaction overnight (18 h) at ambient temperature the solution was desalted by dialysis and subsequently purified again using reversed phase HPLC with a gradient of increasing amount of acetonitrile in 0.1 M triethylammonium acetate pH 7 buffer. Fractions containing the product oligonucleotides were pooled, desalted and formulated in 10 mM Tris, pH 8.0. Purity and optical density were determined.

```
                                               (SEQ ID NO: 4)
Lambda probe 2
5'- JA270 TCG GTA CGG ATA CCG CGA AAG AGC

TWDQ9 PO4 -3'

(SEQ ID NO: 5)
Lambda probe 3
5'- FAM TCG GTA CGG ATA CCG CGA AAG AGC

TWDQ9 PO4 -3'
```

Real-Time PCR Assay

Materials and Methods:

LC480 instrument (96 block) (Roche Applied Science, Cat. no. 04640268001)

LC TaqMaster Roche (Roche Applied Science, Cat no 04535286001)

DNA lambda Roche (Roche Applied Science, Cat. no: 10745782001, [c=6.25 ng/ml])

Lambda reverse Primer: 5'-GTC GCT TTT TGC CCC ACA GTA-3' (SEQ ID NO: 6), BMO 07.442983 Lot ah_PP_48_A12-H12 [c=10 µM] from Example 1

Lambda forward Primer: 5'-AAC AAA AAC GGG GTT TAC CTT A-3' (SEQ ID NO: 1), BMO 07.442982 lot ah_PP_A11-H11 [c=10 µM] from Example 1

3 Lambda probes with different reporter/quencher combinations [c=5 µM] (from Examples 2 and 3):

```
                                               (SEQ ID NO: 3)
5'- R TCG GTA CGG ATA CCG CGA AAG AGC Q PO4 -3'
```

| Oligo name | Oligo no. | 5' modification R | 3' modification Q |
|---|---|---|---|
| Lambda probe 1 | GO2986 | JA270 | BHQ2 |
| Lambda probe 2 | GO3014 | JA270 | TWDQ9 |
| Lambda probe 3 | HO 1214 | FAM | TWDQ9 |

The PCR set up was done according to the LC TaqMaster application manual.

| step | action | | |
|---|---|---|---|
| | component | final conc. | per well and probe |
| 1 | TaqMan Master (5x) | 1x | 4 µl |
| | Primer fwd 10 µM | 0.50 µM | 1 µl |
| | Primer rev 10 µM | 0.50 µM | 1 µl |
| | Probe 5 µM | 0.25 µM | 1 µl |
| | H$_2$O | | 8 µl |
| | total volume | | 15 µl |
| 2 | pipette 15 µl of Mastermix into a well of the LC480 multiwell plate | | |
| 3 | add 5 µl of PCR water or target DNA | | |
| 4 | seal the plate with LC480 sealing foil | | |
| 5 | place the plate in the centrifuge and centrifuge for 2 min at 1500 × g | | |
| 6 | load the plate into the LC480 instrument and start the PCR as described below | | |

Each probe was evaluated with two negative and two positive samples.

PCR Program:

| program | mode | temperature | hold | acquisition | rate |
|---|---|---|---|---|---|
| pre-incubation | activation | 95° C. | 10 min | none | 4.4° C./s |
| amplification | denaturation | 95° C. | 10 s | none | 4.4° C./s |
| | annealing | 60° C. | 30 s | none | 2.2° C./s/45x |
| | extension | 72° C. | 2 s | single | 4.4° C./s |
| cooling | | 37° C. | 30 s | none | 2.2° C./s |

In Examples A and B, real time PCR experiments were carried out using the following probes:

EXAMPLE A

Lambda Hydrolysis Probe 1 (GO 2986):

```
                                               (SEQ ID NO: 3)
5'- X TCG GTA CGG ATA CCG CGA AAG AGC Y PO4-3'
X = JA270  Y = BHQ2
```

Lambda Hydrolysis Probe 2 (GO 3014):

```
                                               (SEQ ID NO: 3)
5'- X TCG GTA CGG ATA CCG CGA AAG AGC Y PO4-3'
X = JA270  Y = TWDQ9
```

EXAMPLE B

Lambda hydrolysis probe 1 (GO 2986):

```
                                               (SEQ ID NO: 3)
5'- X TCG GTA CGG ATA CCG CGA AAG AGC Y PO4-3'
X = JA270  Y = BHQ2
```

Lambda Hydrolysis Probe 2 (GO 3014):

```
                                               (SEQ ID NO: 3)
5'- X TCG GTA CGG ATA CCG CGA AAG AGC Y PO4-3'
X = JA270  Y = TWDQ9
```

Real time PCR experiments were performed in order to obtain a comparison between rhodamine reporter dye JA270 labeled hydrolysis probes which were either quenched by BHQ2 (probe 1) or TWDQ9 (probe 2). Whereas signal background values were very comparable for both probes, both steepness and height of growth curve were superior for the TWDQ9 quenched probe. Cp values for the TWDQ9 quenched probe 2 were better than for BHQ2 quenched probe 1 (cp=21.8 compared to cp=22.0). The table below shows the exact cp values obtained:

| # | Sample | Probe | cp |
|---|---|---|---|
| 1 | Lambda DNA negative | Lambda DNA probe 1 (GO 2986) JA270/BHQ2 | — |
| 2 | Lambda DNA negative | Lambda DNA probe 1 (GO 2986) JA270/BHQ2 | — |
| 3 | Lambda DNA positive | Lambda DNA probe 1 (GO 2986) JA270/BHQ2 | 22.06 |
| 4 | Lambda DNA positive | Lambda DNA probe 1 (GO 2986) JA270/BHQ2 | 22.03 |
| 5 | Lambda DNA negative | Lambda DNA probe 2 (GO 3014) JA270/TWDQ9 | — |
| 6 | Lambda DNA negative | Lambda DNA probe 2 (GO 3014) JA270/TWDQ9 | — |
| 7 | Lambda DNA positive | Lambda DNA probe 2 (GO 3014) JA270/TWDQ9 | 21.80 |
| 8 | Lambda DNA positive | Lambda DNA probe 2 (GO 3014) JA270/TWDQ9 | 21.82 |

EXAMPLE C

A real time PCR experiment was also performed with a fluorescein reporter dye labeled hydrolysis probe quenched by TWDQ9 with the following sequence:
Lambda Hydrolysis Probe 3 (HO 1214):

```
                                          (SEQ ID NO: 3)
5'- X TCG GTA CGG ATA CCG CGA AAG AGC Y PO4-3'
X = FAM Y = TWDQ9
```

Good growth curves could be obtained. Cp values obtained were comparable to JA270/TWDQ9 labeled hydrolysis probe 2. The table below shows the exact cp values obtained:

| # | sample | Probe | cp |
|---|---|---|---|
| 1 | Lambda DNA negative | Lambda DNA probe 3 (HO1214) FAM/TWDQ9 | — |
| 2 | Lambda DNA negative | Lambda DNA probe 3 (HO1214) FAM/TWDQ9 | — |
| 3 | Lambda DNA positive | Lambda DNA probe 3 (HO1214) FAM/TWDQ9 | 21.83 |
| 4 | Lambda DNA positive | Lambda DNA probe 3 (HO1214) FAM/TWDQ9 | 21.81 |

The result demonstrates that the quencher also can be combined with different reporter dyes.

What is claimed is:

1. A compound represented by the formula

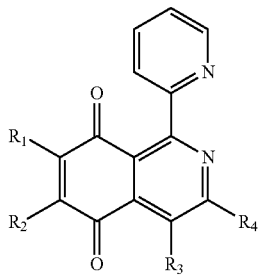

wherein
either $R_1$ or $R_2$ is hydrogen, a C1-C6 alkyl, or a halogen, and the other of $R_1$ of $R_2$ is -Q-Y, where Q is a straight or branched, saturated or unsaturated, substituted or unsubstituted C1-C10 hydrocarbon where Y is selected from the group consisting of hydroxyl, carboxyl, and amino, and
$R_3$ and $R_4$ are —$NR_5R_6$, where $R_5$ and $R_6$ are hydrogen or a substituted or unsubstituted aryl.

2. The compound of claim 1, wherein Q is a straight or branched, saturated or unsaturated, substituted or unsubstituted C2-C8 hydrocarbon.

3. The compound of claim 1, wherein Y is hydroxyl or carboxyl.

4. The compound of claim 1, wherein $R_3$ or $R_4$ is —$NR_5H$.

5. The compound of claim 1, wherein $R_3$ and $R_4$ is —$NR_5H$.

6. The compound of claim 1, wherein each of $R_3$ and $R_4$ is —$NR_5R_6$.

7. The compound of claim 6, wherein $R_5$ is a substituted or unsubstituted aryl.

8. The compound of claim 7, wherein the substituted or unsubstituted aryl is phenyl or toluyl.

9. The compound of claim 1, wherein the aryl is an aromatic $C_6H_5$, $C_{10}H_7$, or $C_{14}H_9$ hydrocarbon residue.

10. The compound of claim 1, wherein either $R_1$ or $R_2$ is a 1-hydroxy-4-ethyl-butyl residue or an n-pentanoic acid residue and the other of $R_1$ of $R_2$ is hydrogen, and $R_5$ is a 4-toluyl or a phenyl residue.

11. The compound of claim 1, wherein Y is capable of binding to a solid support or to a biomolecule.

12. The compound of claim 1, wherein the compound is coupled to a solid support via -Q-Y.

13. The compound of claim 1, wherein the compound is coupled to a biomolecule via -Q-Y.

14. A method of producing a compound represented by the formula

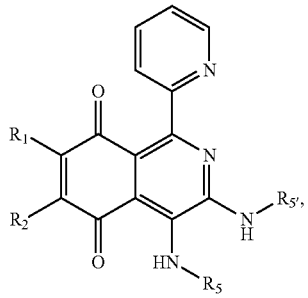

the method comprising the steps of:

a) reacting a disubstituted oxalic acid diamide of the formula $R_5$—N=C(OH)—C(OH)=N—$R_{5'}$, with phosphorous pentachloride to obtain a bis-imidoyl chloride of oxalic acid of the formula $R_5$—N=CCl—ClC=N—$R_{5'}$, b) reacting the bis-imidoyl chloride of oxalic acid obtained in step a) with 2-amino methylpyridine to obtain a disubstituted pyrido[1,2-a]pyrazine of Formula III

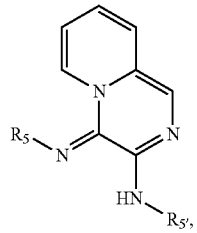

(III)

and c) reacting the disubstituted pyrido[1,2-a]pyrazine obtained in step b) with a monosubstituted chinone of Formula IV

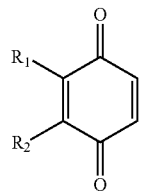

(IV)

to obtain the compound of Formula II, wherein either $R_1$ or $R_2$ is hydrogen, a C1-C6 alkyl or a halogen and the other of $R_1$ or $R_2$ is -Q-Y, where Q is a straight or branched, saturated or unsaturated, substituted or unsubstituted C1-C10 hydrocarbon where Y is selected from the group consisting of hydroxyl, carboxyl, and amino, and $R_3$ and $R_4$ are —$NR_5R_6$ or —$NR_5R_6$, where $R_5$, $R_{5'}$, and $R_6$ are hydrogen or a substituted or unsubstituted aryl.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aacaaaaacg gggtttacct ta                                            22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcgcttttt gctgtcccac agta                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tcggtacgga taccgcgaaa gagc                                          24
```

-continued

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tcggtacgga taccgcgaaa gagc                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
tcggtacgga taccgcgaaa gagc                                              24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtcgcttttt gccccacagt a                                                 21
```